(12) United States Patent
Hayashida

(10) Patent No.: US 7,856,085 B2
(45) Date of Patent: Dec. 21, 2010

(54) X-RAY IMAGING APPARATUS

(75) Inventor: Shinsuke Hayashida, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/534,746

(22) Filed: Aug. 3, 2009

(65) Prior Publication Data

US 2010/0034356 A1  Feb. 11, 2010

(30) Foreign Application Priority Data

Aug. 5, 2008  (JP) .............................. 2008-201430

(51) Int. Cl.
  *H05G 1/30* (2006.01)
(52) U.S. Cl. ...................................................... 378/98
(58) Field of Classification Search .................. 378/98, 378/62, 116, 154, 4, 98.8, 19; 382/132, 195
  See application file for complete search history.

(56) References Cited

U.S. PATENT DOCUMENTS

| 5,040,201 A | 8/1991 | Slump |
| 7,006,600 B1 * | 2/2006 | Krema et al. .............. 378/98.7 |
| 7,550,733 B2 * | 6/2009 | Endo et al. ............. 250/370.09 |
| 2004/0114725 A1 | 6/2004 | Yamamoto |
| 2004/0146190 A1 | 7/2004 | Kasai |
| 2006/0242094 A1 | 10/2006 | Tamakoshi |
| 2007/0253534 A1 | 11/2007 | Abe |

FOREIGN PATENT DOCUMENTS

| FR | 2910266 | 6/2008 |
| JP | 2001-276032 A | 10/2001 |
| JP | 3105520 B | 11/2003 |
| JP | 2005-046203 A | 2/2005 |
| JP | 2005-312949 A | 11/2005 |

* cited by examiner

*Primary Examiner*—Irakli Kiknadze
(74) *Attorney, Agent, or Firm*—Canon U.S.A., Inc. I.P. Division

(57) ABSTRACT

First, a connection state is detected. Next, a determination is made as to whether a connection is made via a dedicated line. If it is determined that the connection is not made via a dedicated line, image accumulation time is calculated. Then, after drive timing is changed, an imaging operation is started.

8 Claims, 10 Drawing Sheets

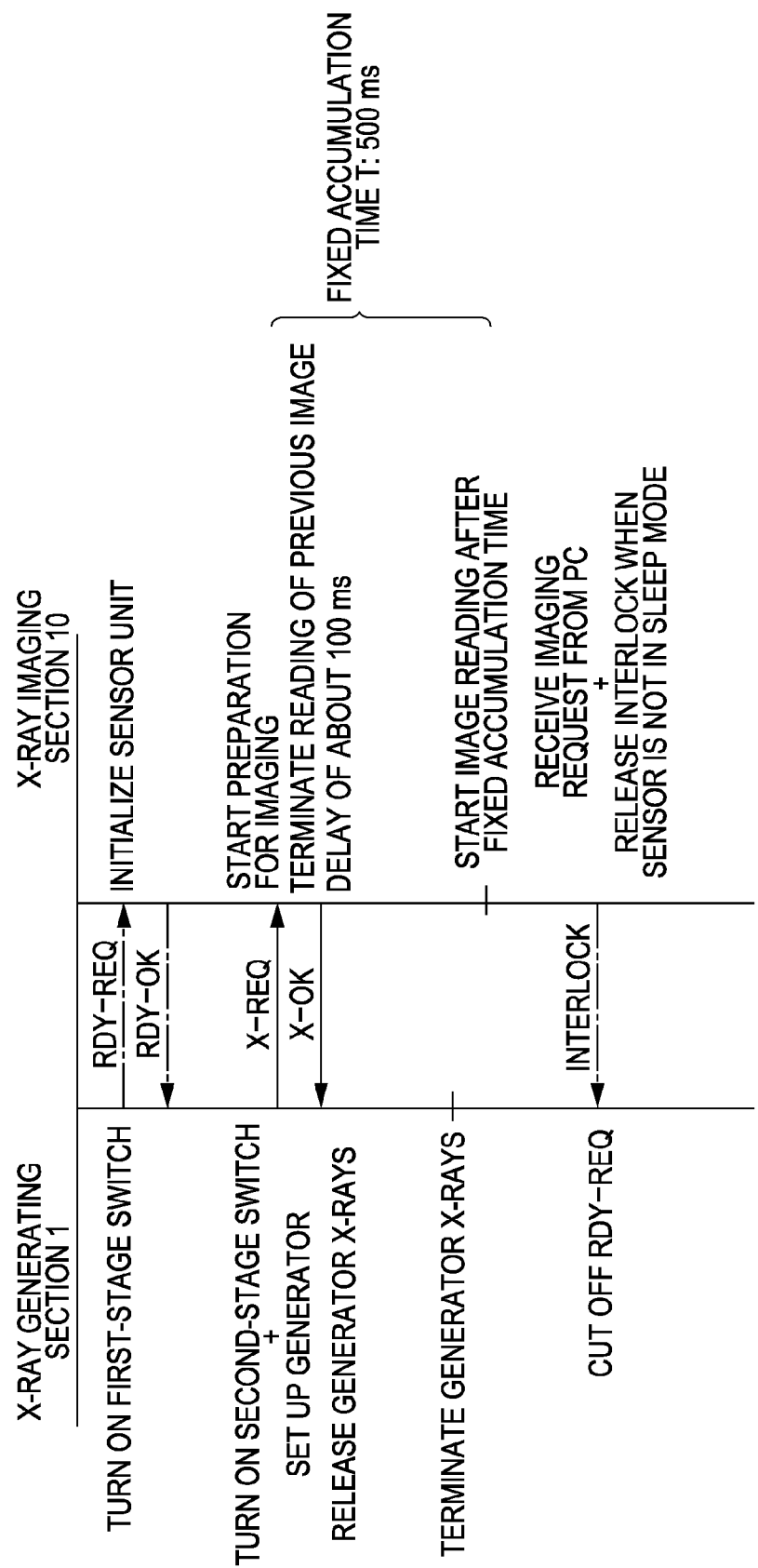

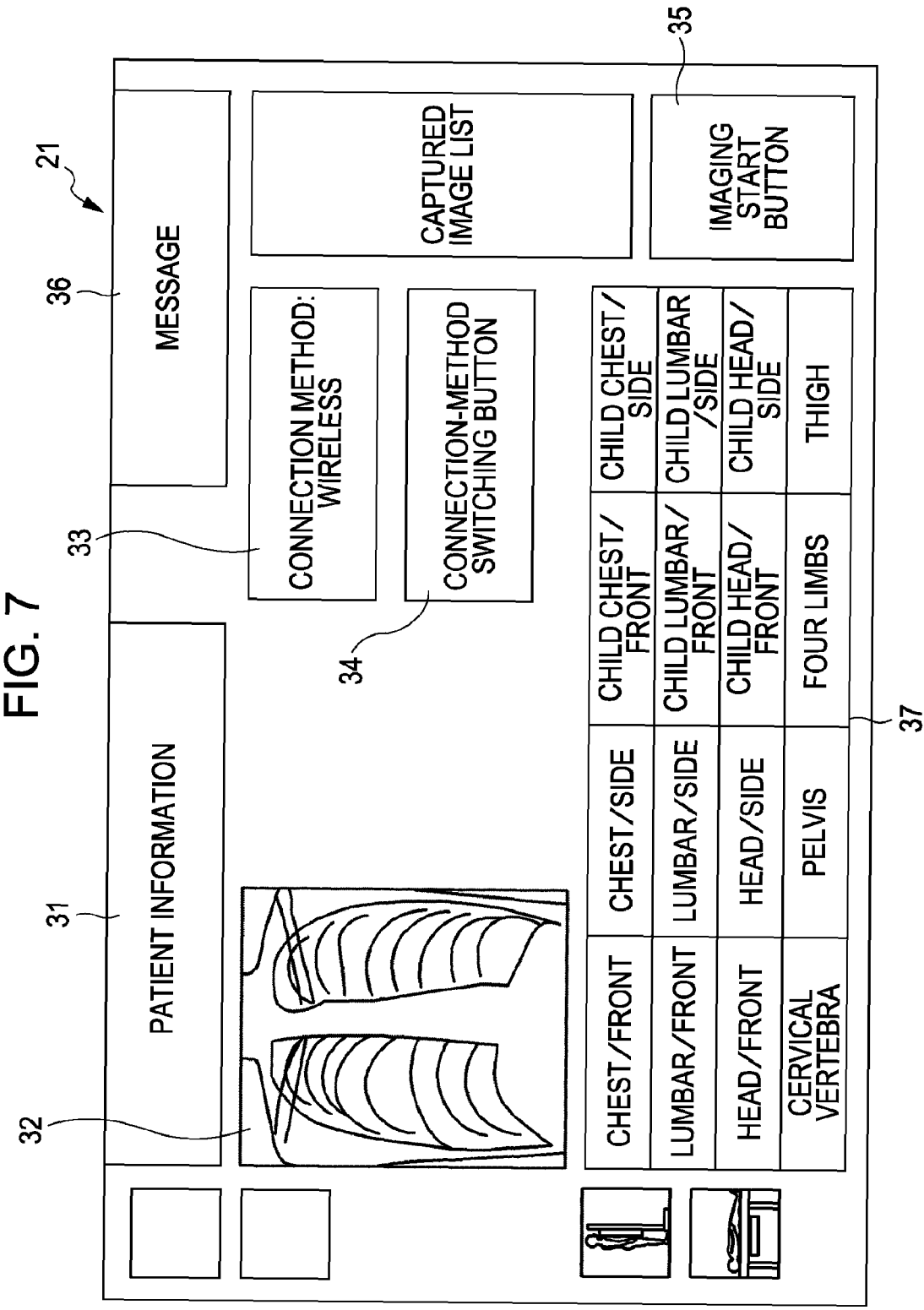

CHEST IMAGING APPARATUS

BUCKY UPRIGHT IMAGING STAND

BUCKY TABLE (TOP PLATE LIFTING TYPE)

BUCKY IMAGING APPARATUS (DU ALARM TYPE)

X-RAY IMAGING APPARATUS

BACKGROUND OF THE INVENTION

1. Field of the Invention

The present invention relates to X-ray imaging apparatuses capable of capturing an X-ray image of a subject.

2. Description of the Related Art

For X-ray imaging for medical diagnostic purposes, digital imaging apparatuses in which an imaging unit including a photoelectric conversion element performs imaging have been widely used in recent years. Such a digital imaging apparatus is capable of producing an X-ray image without developing a film etc., and thus is advantageous in terms of immediacy over an imaging apparatus using a film.

In a known X-ray imaging apparatus including a photoelectric conversion element, an imaging unit and an X-ray generating unit are connected to each other via a dedicated line. This allows communication of drive timing signals and timing signals for X-ray generation, as well as power and image information, between the imaging unit and the X-ray generating unit.

In an X-ray imaging apparatus having an imaging unit including a photoelectric conversion element, after X-ray radiation, electrons converted by X-rays are read from the photoelectric conversion element. Thus, an image representing a distribution of transmittance of x-rays radiated during a specific period of time is produced.

There are broadly two different patterns of timing for reading out electrons. In one method, an X-ray generating unit transmits readout timing to an X-ray imaging unit for synchronization therebetween. Specifically, after completion of X-ray radiation, the X-ray generating unit transmits an X-ray radiation completion signal to the X-ray imaging unit. Upon receipt of the X-ray radiation completion signal, the X-ray imaging unit terminates accumulation of electric charge and starts reading out electrons.

In another method, as described in Japanese Patent Laid-Open No. 2005-46203, an X-ray generating unit radiates X-rays during a period of time in which it is permitted to radiate X-rays. Then, after receipt of an X-ray generation signal, an X-ray imaging unit reads out an image during a fixed period of image accumulation time.

In Japanese Patent Laid-Open No. 2005-46203, in response to instructions from a first switch to prepare for X-ray imaging, the X-ray generating unit and the X-ray imaging unit start preparing for imaging. Then, accumulation of electric charge is started. Here, a time delay may occur depending on the method for connection between the X-ray generating unit and the X-ray imaging unit.

Generally, a connection between an X-ray imaging unit and an X-ray generating unit can be made via a general-purpose line or a wireless connection, as well as via a dedicated line. As long as necessary functions are provided, a connection using a general-purpose line or a wireless connection is advantageous over a connection using a dedicated line, in terms of usability and cost. Examples of general-purpose lines include Ethernet (registered trademark) and Gigabit Ethernet (registered trademark). Examples of wireless connections include a wireless local area network (LAN) connection and a connection which allows communication using low and high frequency electromagnetic waves, such as those used in dedicated short-range communication.

However, when a connection method other than that using a dedicated line is used, that is, for example, when a wireless connection is used, external factors including transmissibility of electromagnetic waves may prevent the connection from being established at one time. As a result, many retries for the connection may cause a time delay. When a network line is used, line congestion may reduce communication speed and may also cause a time delay. Reasons for using a connection method other than a dedicated wired connection, that is, reasons for using a wireless connection or the like are that digital X-ray imaging apparatuses are demanded to achieve improved usability and reduced cost, as well as high-quality images.

In a known X-ray imaging apparatus having a fix period of accumulation time, there may be a period of time in which signals cannot be accumulated during X-ray radiation. That is, there may be a period of time in which unnecessary x-ray radiation takes place. In other words, the known X-ray imaging apparatus does not optimize the timing control of imaging drive signals in accordance with different conditions.

Japanese Patent Laid-Open No. 2005-46203 discloses a control method for controlling an X-ray imaging operation performed by the X-ray generating unit and the X-ray imaging unit. The X-ray generating unit generates X-rays, while the X-ray imaging unit accumulates electric charge corresponding to the amount of the X-rays and outputs an electric signal. This control method causes the X-ray generating unit to prepare for X-ray generation in accordance with an instruction to prepare for X-ray imaging. The control method includes the steps of starting accumulation of electric charge after the X-ray imaging unit completes preparation for X-ray imaging, generating X-rays in accordance with an instruction to perform X-ray imaging, and terminating the accumulation of electric charge and the generation of X-rays when a predetermined period of time has elapsed since the start of accumulation of electric charge.

However, Japanese Patent Laid-Open No. 2005-46203 does not provide a means for changing the time for terminating the accumulation of electric charge depending on the connection method, accumulation time, and information about a region whose image is to be captured.

An X-ray imaging apparatus disclosed in Japanese Patent No. 3105520 includes an image recording device and a synchronizing device. The image recording device applies a recording pulse to the synchronizing device, which adjusts synchronization of an X-ray source to changes in periodical operation.

In the technique disclosed in Japanese Patent No. 3105520, the X-ray imaging apparatus transmits an imaging drive signal for synchronization of the X-ray source. However, there is no means for changing the drive method, such as timing of the imaging drive signal, depending on the connection method etc.

Japanese Patent Laid-Open No. 2001-276032 discloses an imaging apparatus that has a configuration for preventing degradation of image quality caused by vibrations and electromagnetic noise resulting from grid movement. With this configuration, the imaging apparatus is capable of capturing high-quality images most suitable for medical diagnosis. In this imaging apparatus, after a drive operation for driving the movement of a movable grid is stopped, a readout operation for reading out an accumulation signal of an image pickup element is started.

However, in the imaging apparatus disclosed in Japanese Patent Laid-Open No. 2001-276032, the accumulation of electric charge is terminated after the moving grid is stopped. There is no means for changing the time for terminating the accumulation of electric charge depending on the connection method, accumulation time, and information about a region whose image is to be captured.

A radiation imaging apparatus disclosed in Japanese Patent Laid-Open No. 2005-312949 includes a conversion circuit unit in which a plurality of pixels including conversion elements are arranged in an array on a substrate, a readout circuit unit configured to read out a signal from the conversion circuit unit, and a radiation generation switch used to instruct a radiation generating unit to emit radiation. An imaging operation period for capturing a radiation image includes two operation periods: an idling operation period before emission of radiation, and a reading operation period starting at the time of emission of radiation. To enable the operator to operate the radiation generation switch at appropriate time immediately after the end of the idling operation period, the radiation imaging apparatus generates an emission stimulating signal to the operator during the idling operation period.

The radiation imaging apparatus disclosed in Japanese Patent Laid-Open No. 2005-312949 has no means to change the drive method, such as accumulation time, depending on the connection method etc. However, if an X-ray imaging apparatus including a photoelectric conversion element performs communication using a connection method other than a connection method using a dedicated line, synchronization with an X-ray generating unit may be lost or radiation may take place during a period of time in which image accumulation is not performed.

In an X-ray imaging apparatus that performs a reading operation during image accumulation time, the above problems may be solved by significantly increasing the image accumulation time. However, as the image accumulation time increases, dark current noise of a photoelectric conversion element increases and, as a result, image quality may be adversely affected.

SUMMARY OF THE INVENTION

The present invention provides an X-ray imaging apparatus capable of solving the problems described above. That is, the present invention provides an X-ray imaging apparatus capable of preventing unnecessary X-ray radiation caused by communication delay depending on the communication method, while reducing image accumulation time in an imaging unit.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate exemplary embodiments of the invention, and together with the description, serve to explain the principles of the invention.

FIG. 6 illustrates a sequence in a known X-ray imaging apparatus.

FIG. 7 is a front view of an operation panel.

DESCRIPTION OF THE EXEMPLARY EMBODIMENTS

Embodiments of the present invention will be described in detail in accordance with the accompanying drawings.

Figure 1:
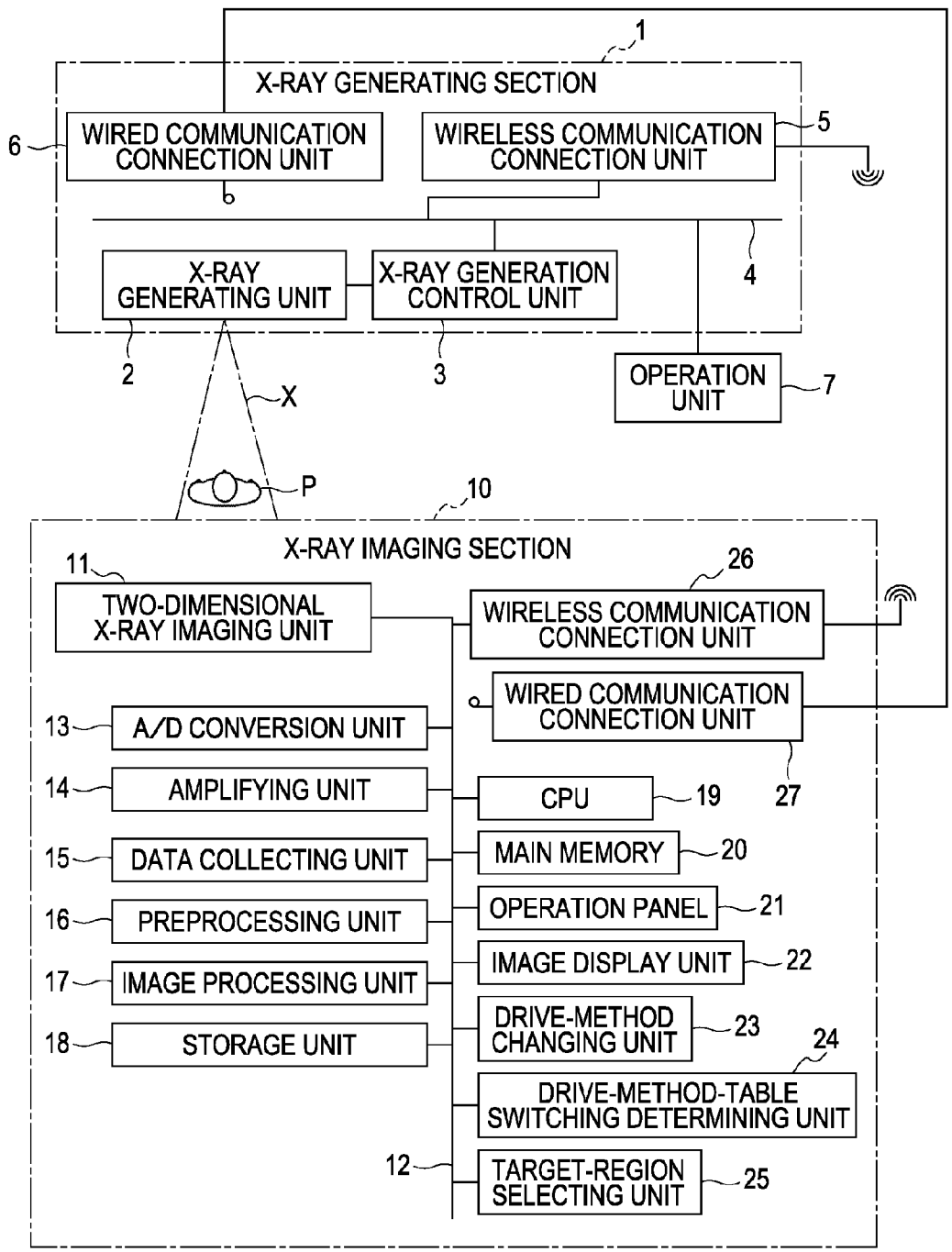
FIG. 1 is a block diagram illustrating a circuit configuration of an X-ray imaging apparatus according to a first exemplary embodiment of the present invention.

FIG. 1 is a block diagram illustrating a circuit configuration of an entire X-ray imaging apparatus according to a first exemplary embodiment of the present invention. The X-ray imaging apparatus includes an X-ray generating section 1 that generates X-rays, and an X-ray imaging section 10 on which X-rays having passed through a subject P is incident. The X-ray generating section 1 and the X-ray imaging section 10 are arranged opposite each other.

The X-ray generating section 1 includes an X-ray generating unit 2 that generates X-rays. The X-ray generating unit 2 is connected to an X-ray generation control unit 3. A plurality of communication connection units, that is, a wireless communication connection unit 5 for wireless communication with the X-ray imaging section 10 and a wired communication connection unit 6 for wired communication with the X-ray imaging section 10 are connected to the X-ray generation control unit 3 via a bus 4. An operation unit 7 for operating the X-ray generating section 1 via the bus 4 is connected to the X-ray generating section 1.

The X-ray imaging section 10 includes a two-dimensional X-ray imaging unit 11 including a photoelectric conversion element that receives X-rays having passed through the subject P. The two-dimensional X-ray imaging unit 11 is connected through a central processing unit (CPU) bus 12 to an analog-to-digital (A/D) conversion unit 13, an amplifying unit 14, a data collecting unit 15 that collects captured image data, and a preprocessing unit 16 that preprocesses an image obtained by the data collecting unit 15. An image processing unit 17, a storage unit 18 that stores an image, a CPU 19, a main memory 20, an operation panel 21, an image display unit 22, a drive-method changing unit 23, a drive-method-table switching determining unit 24, and a target-region selecting unit 25 are connected to the CPU bus 12.

A plurality of communication connection units, that is, a wireless communication connection unit 26 and a wired communication connection unit 27 for communicating with the X-ray generating section 1 are also connected to the CPU bus 12.

The main memory 20 stores various types of data necessary for processing in the CPU 19. At the same time, the main memory 20 functions as a working memory for the CPU 19. The CPU 19 uses the main memory 20 to control an overall operation of the X-ray imaging apparatus in accordance with an operation on the operation panel 21.

The X-ray imaging section 10 communicates through the wireless communication connection unit 26 or the wired communication connection unit 27 with the wireless communication connection unit 5 or the wired communication connection unit 6 in the X-ray generating section 1, for example, every 10 minutes. Thus, the X-ray imaging section 10 indicates, on the operation panel 21, a communication connection unit used to perform imaging. When an operator inputs imaging instructions from the operation panel 21, the imaging instructions are displayed on the operation panel 21 as well as being stored in the storage unit 18.

When giving imaging instructions, the operator uses the target-region selecting unit 25 on the operation panel 21 to select a specific region whose image is to be captured (hereinafter referred to as "target region"). The imaging instructions are transmitted by the CPU 19 via the CPU bus 12 to the drive-method changing unit 23. Upon receipt of the imaging instructions, the drive-method changing unit 23 changes a drive method through the drive-method-table switching determining unit 24.

Then, when the operator uses the operation unit 7 in the X-ray generating section 1 to give an instruction to generate X-rays, the X-ray generating section 1 controls the X-ray generating unit 2 through the X-ray generation control unit 3 to perform X-ray imaging by radiating X-rays.

In this X-ray imaging, X-rays radiated from the X-ray generating unit 2 pass through the subject P while attenuating, and reach the two-dimensional X-ray imaging unit 11. Then, the two-dimensional X-ray imaging unit 11 outputs an X-ray image signal. In the first exemplary embodiment, the subject P is a human body. This means that an X-ray image output from the two-dimensional X-ray imaging unit 11 is a human body image.

The X-ray image signal output from the two-dimensional X-ray imaging unit 11 is converted into a predetermined digital signal by the A/D conversion unit 13, and transferred as X-ray image data to the preprocessing unit 16. Primarily, the preprocessing unit 16 corrects characteristics of the X-ray imaging apparatus. The preprocessing unit 16 performs gain correction on the X-ray image data to correct variations in sensitivity among pixels of the two-dimensional X-ray imaging unit 11. Additionally, the preprocessing unit 16 performs dark current correction on the X-ray image data to correct variations in dark current among pixels of the two-dimensional X-ray imaging unit 11. Before the operator performs X-ray imaging, the preprocessing unit 16 stores, in the main memory 20, a gain correction image for use in gain correction and a dark-current correction image for use in dark current correction. The stored images are called by the preprocessing unit 16 when necessary for correction.

The X-ray image data preprocessed by the preprocessing unit 16 is transferred, as original image data, via the CPU bus 12 to the main memory 20 and the image processing unit 17 under the control of the CPU 19. After the characteristics of the X-ray imaging apparatus are corrected, the image processing unit 17 performs image processing on the X-ray image data for better viewing of information that a doctor wants to observe. Examples of the image processing include noise reduction, frequency processing, and gradation processing depending on the type of display medium, such as a monitor or a film. The X-ray image data subjected to the image processing is output to the image display unit 22.

Figure 2:
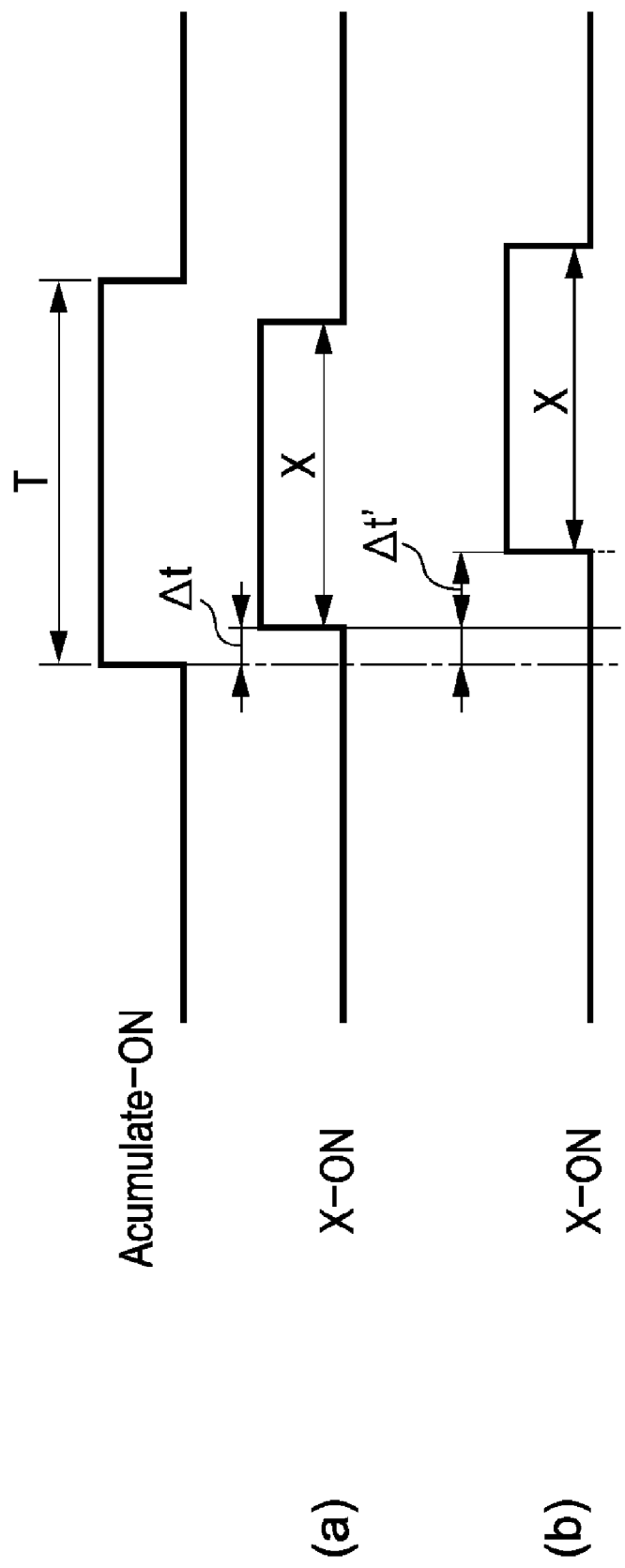
FIG. 2 is a timing diagram of a known X-ray imaging apparatus.
Figure 3:
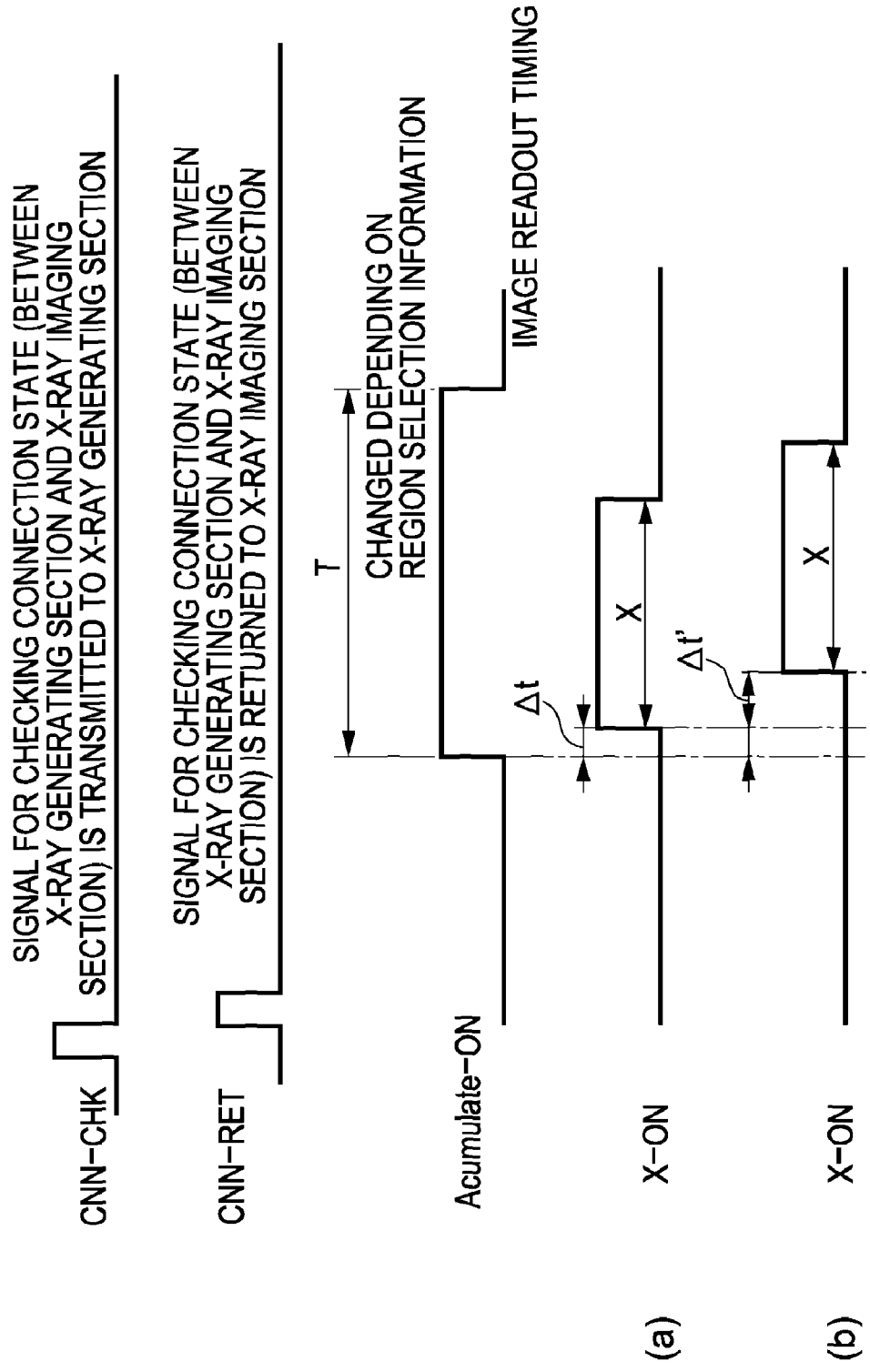
FIG. 3 is a timing diagram of the X-ray imaging apparatus according to the first exemplary embodiment.

FIG. 2 is a timing diagram of a known X-ray imaging operation. FIG. 3 is a timing diagram of an X-ray imaging operation according to the first exemplary embodiment. The present exemplary embodiment will be described by comparison of FIG. 2 and FIG. 3.

In (a) of FIG. 2, normal X-ray delay time $\Delta t$ and X-ray radiation time X (X-ON time) can fall within image accumulation time T (Accumulate-ON time) which starts from the time when the two-dimensional X-ray imaging unit 11 starts accumulating electric charge to the time when the two-dimensional X-ray imaging unit 11 starts reading out the electric charge.

However, when a different connection method is used, as illustrated in (b) of FIG. 2, delay time $\Delta t'$ caused by communication retries etc. occurs in addition to the normal X-ray delay time $\Delta t$. In this case, even when X-rays are radiated, it may not be possible to obtain an image, because the image accumulation time T already ends.

As a solution to this, as illustrated in FIG. 3, signals (CNN-CHK and CNN-RET) for checking the connection state are communicated in advance, between the X-ray generating section 1 and the X-ray imaging section 10 in the first exemplary embodiment.

For example, the connection states on the network layer and other lower layers in the open systems interconnection (OSI) reference model are obtained. The OSI reference model includes the physical layer, the data-link layer, the network layer, the transport layer, the session layer, the presentation layer, and the application layer. Most basically, the connection state on the physical layer is checked as to which of a dedicated line, a general-purpose line (Ethernet etc.), and a wireless connection (wireless LAN, IEEE802.11a, etc.) is used. The physical layer primarily deals with transmission of a raw bitstream through a physical transfer medium. In the case of a wireless LAN, free space serves as a transfer medium. The physical layer defines a date rate, a modulation method, signal system parameters, and parameters for synchronization between a transmitter and a receiver.

The X-ray imaging apparatus of the first exemplary embodiment checks the connection state as described above and displays the current connection state on the operation panel 21. Even when there is a plurality of possible connection methods, the X-ray imaging apparatus selects one of them. This is because the purpose of checking the connection state in the first exemplary embodiment is to determine the possibility and degree of communication delay to prevent unnecessary X-ray radiation.

In the first exemplary embodiment, there is provided a table for changing the image accumulation time T depending on the detected connection state. For example, when the connection is made through a method, such as a wireless connection, having relatively low communication stability, the delay time $\Delta t'$ caused by communication retries etc. may be increased depending on the external environment. Even when the delay time $\Delta t'$ occurs, the image accumulation time T can be changed depending on the connection state. Therefore, it is possible to reduce possibility that X-rays will be radiated outside the image accumulation time T.

As a method to ensure that image accumulation is reliably performed during X-ray radiation, it may be possible to increase the normal image accumulation time T. However, as the image accumulation time T increases, the level of noise called dark current noise increases. Typically, in the two-dimensional X-ray imaging unit 11 including a photoelectric conversion element, the degree of variations in dark current noise increases as the image accumulation time T increases. Therefore, to improve image quality, it is necessary to reduce the image accumulation time T as much as possible.

Figure 4:
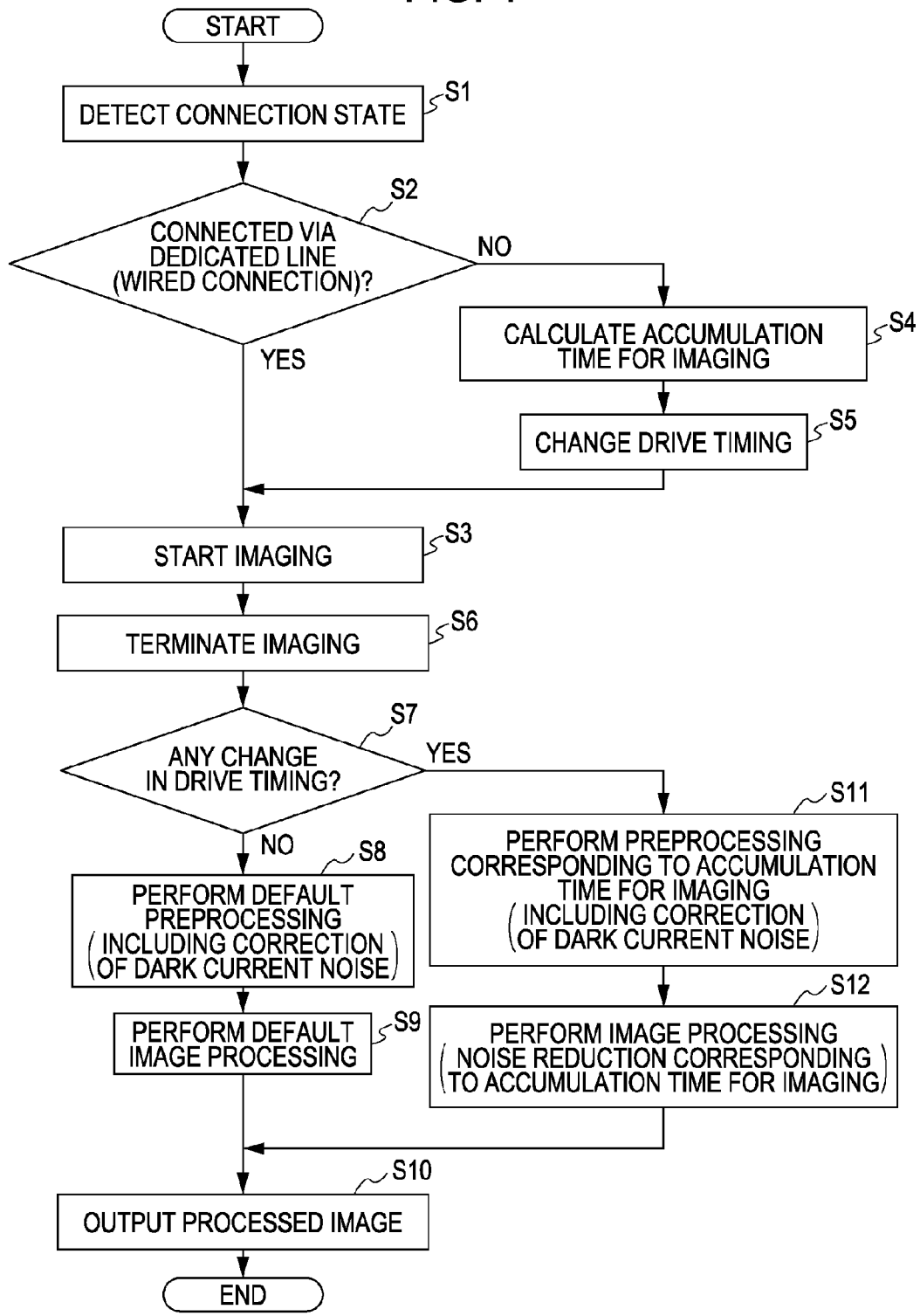
FIG. 4 is a flowchart of the first exemplary embodiment.

FIG. 4 is a flowchart of an X-ray imaging operation. In step S1, a connection state is detected by a detecting unit that detects a communication method of a communication connection unit. It is desirable that the connection state be obtained every time immediately before an imaging operation is performed. However, if the connection state is obtained for every imaging operation, the time required for one imaging operation increases. For example, in facilities frequently visited by patients for health checkups, it may be useless to check the connection state for every imaging operation in an environment where there is little change in connection state. Therefore, for imaging operations for health checkup purposes, it is desirable to make it possible to check the connection state every predetermined period of time (e.g., every 10 minutes), rather than every time an imaging operation is performed.

In step S2, on the basis of the connection state detected in step S1, a determination is made as to whether the connection is a wired connection via a dedicated line. If it is determined that the connection is a wired connection via a dedicated line (Yes in step S2), it can be predicted that the stability of communication will be maintained without significant deviation from a known value. Therefore, without changing default drive timing, the process proceeds to step S3 to start an imaging operation. On the other hand, if it is determined in step S2 that the connection is not a wired connection via a dedicated line (No in step S2), since the stability of communication may differ from that in the case of a dedicated line, the process proceeds to step S4.

After the image accumulation time T for the imaging operation is calculated in step S4, the process proceeds to step S5. On the basis of the image accumulation time T obtained in step S4, the drive timing is changed in step S5. Specifically, signal readout timing is delayed in step S5. Then, the process proceeds to step S3.

In step S3, the imaging operation starts at the determined drive timing. The corresponding sequence will be described below, but upon completion of preparation for the imaging operation, the X-ray imaging section 10 outputs a preparation completion signal to the X-ray generating section 1. After receipt of the preparation completion signal, when an X-ray radiation button (not shown) is pressed, the X-ray generating section 1 outputs an X-ray generation signal to the X-ray imaging section 10. After the X-ray imaging section 10 receives the X-ray generation signal, the X-ray generating section 1 generates X-rays. After the X-ray generation signal is received, the two-dimensional X-ray imaging unit 11 in the X-ray imaging section 10 reads out an image during the image accumulation time T determined as described above.

Upon completion of the imaging operation in step S3, the process proceeds to step S6. In step S6, the imaging operation is terminated, for example, by interlocking the X-ray generation. In step S7, a determination is made as to whether the drive timing has been changed for the captured image. If there has been no change in drive timing (No in step S7), the process proceeds to step S8. In step S8, the preprocessing unit 16 performs default preprocessing, for example, in an accumulation time of 500 ms. In step S9, the image processing unit 17 performs default image processing. In step S10, the image processed in step S9 is output to a medium, such as a film or a monitor, specified in advance by the operator on the operation panel 21.

If it is determined in step S7 that there has been a change in drive timing (Yes in step S7), the process proceeds to step S11. In step S11, preprocessing corresponding to the image accumulation time T for the imaging operation is performed. Unlike the default preprocessing of step S8, dark current correction is performed in the preprocessing of step S11. This is because when the image accumulation time T is changed by the change in drive timing, the amount of dark current is changed accordingly. That is, a dark current image has characteristics depending on the image accumulation time T. Therefore, to improve image quality, it is desirable that correction be performed on a dark current image corresponding to the same image accumulation time T.

If it is determined in step S7 that there has been a change in drive timing, unlike the default image processing of step S9, noise reduction corresponding to the image accumulation time T for the imaging operation is performed. To avoid unnecessary X-ray radiation, the drive timing is changed to increase the image accumulation time T. As the image accumulation time T increases, the level of noise in an image increases. The present exemplary embodiment involves noise reduction including frequency processing. When the drive timing is changed and the image accumulation time T is increased, there is performed frequency processing in which emphasis coefficients corresponding to specific frequency images are emphasized in noise reduction.

In the two-dimensional X-ray imaging unit 11 including a photoelectric conversion element, there are broadly two different patterns of timing for obtaining a dark current image. One is to capture a dark current image immediately after an X-ray image is obtained. The other is to obtain dark current images, in advance, over several cycles of the image accumulation time T. In the former method, capturing a still image involves additional time required to obtain only one image before image display, but capturing a moving image involves additional time required to obtain a plurality of images before image display. On the other hand, in the latter method, it is necessary to store, in advance, a plurality of dark current images corresponding to the corresponding accumulation. In this case, since it is not necessary to obtain a dark current image after an X-ray image is obtained, the latter method is advantageous over the former method in terms of the speed of image display.

Any method for obtaining a dark current image can be used in the present exemplary embodiment. Dark current correction is made by subtracting, from an X-ray image, a dark current image corresponding to the image accumulation time T for the X-ray image. The dark current correction is followed by gain correction. Thus, an image in which photoelectric conversion characteristics are corrected is output.

Upon completion of the preprocessing in step S11, the process proceeds to step S12, where image processing is performed. Then, in step S10, the image processed in step S11 is output to a medium, such as a film or a monitor, specified in advance by the operator on the operation panel 21.

Figure 5:
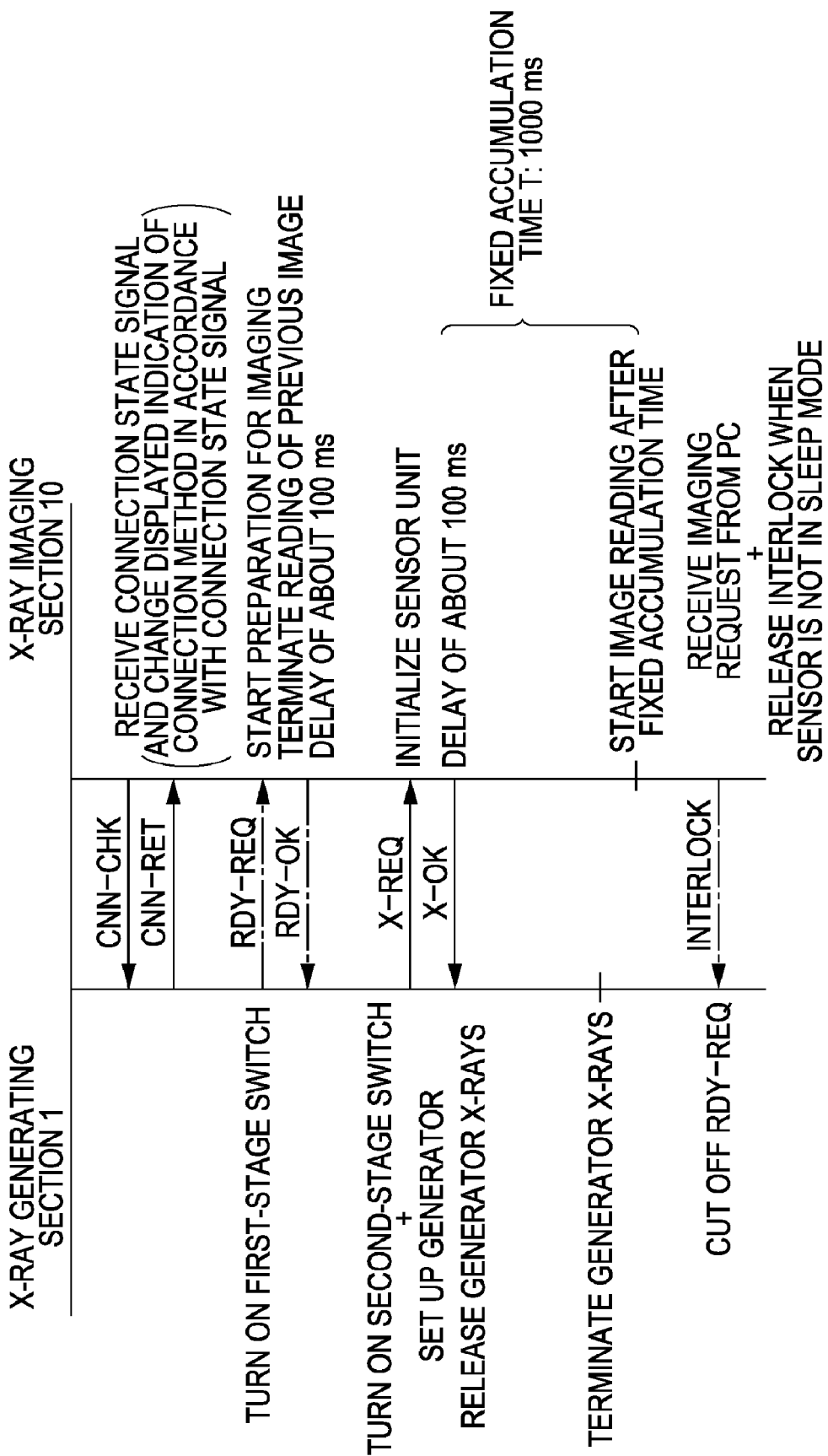
FIG. 5 illustrates a sequence in the X-ray imaging apparatus of the first exemplary embodiment.

FIG. 5 illustrates a sequence between the X-ray generating section 1 and the X-ray imaging section 10 according to the first exemplary embodiment. FIG. 6 illustrates a known sequence. The sequence of the present exemplary embodiment will be described by comparison of FIG. 5 and FIG. 6.

In the present exemplary embodiment, the X-ray imaging section 10 knows a connection state. The X-ray imaging section 10 transmits a signal (CNN-CHK) for checking the connection state to the X-ray generating section 1, and receives a signal (CNN-RET) returned from the X-ray generating section 1. For example, when an operating system (OS) of the X-ray imaging section 10 is Windows (registered trademark) (or MS-DOS) or Linux, transmitting a packet internet groper (ping) command makes it possible to obtain a statistical result of communication trials.

A purpose of the present sequence is to check the stability of communication in the connection state. Therefore, in the present exemplary embodiment, commands on Windows (or MS-DOS), such as winipcfg, arp, traceroute, netstat, ipconfig, route, and telnet, may be used. It is desirable to check the communication state on an application actually used by the X-ray imaging section 10. For example, IP-level information that can be checked with the ping command, that is, information at the network layer of the OSI reference model can also be used in the first exemplary embodiment.

Next, the operator places the subject P between the X-ray generating section 1 and the X-ray imaging section 10. After saying, for example, "Take a deep breath and hold it" to inform the subject P of the start of imaging, the operator turns on a first-stage switch of the X-ray generating section 1. The X-ray generating section 1 transmits an RDY-REQ signal to the X-ray imaging section 10. The X-ray imaging section 10 stops reading out the previous image and starts preparing for imaging. A sensor which requires dummy reading drives dummy reading.

Then, for example, after a delay of about 100 ms, the X-ray imaging section 10 transmits an RDY-OK signal to the X-ray generating section 1 to permit the X-ray generating section 1 to turn on a second-stage switch. After the operator turns on the second-stage switch of the X-ray generating section 1, the X-ray generating section 1 transmits an X-REQ signal to the X-ray imaging section 10 and sets up a generator. Upon receipt of the X-REQ signal, the X-ray imaging section 10 initializes the two-dimensional X-ray imaging unit 11 serving as a sensor unit. After a delay of about 100 ms, the X-ray imaging section 10 transmits an X-OK signal to the X-ray generating section 1, so that generator X-rays are released.

In related art, the X-ray generating section 1 and the X-ray imaging section 10 are wired to each other via a dedicated line and the stability of the communication is ensured. Therefore, for example, as illustrated in FIG. 6, when the image accumulation time T is 500 ms, it is quick enough to start image reading after the fixed time of 500 ms. However, in the first exemplary embodiment, in the case of an external environment where stability of communication is impaired, if a delay in communication time occurs due to, for example, collision or waiting time in communication of the X-OK signal, the timing of releasing generator X-rays will be delayed.

In consideration of such a situation in communication, in the first exemplary embodiment, the X-ray imaging apparatus has a setting table for setting the image accumulation time T in accordance with a communication method and a target region.

FIG. 5 illustrates a sequence performed when the image accumulation time T is set to 1000 ms. The X-ray generating section 1 instructs the X-ray imaging section 10 to start image reading after the elapse of the image accumulation time T. In response to an imaging request from a personal computer (PC) or the operator, the X-ray imaging section 10 releases an interlock in a state where the sensor is not in a sleep mode. Then, the X-ray imaging section 10 transmits an interlock signal to the X-ray generating section 1, where the RDY-REQ signal is cut off.

FIG. 7 illustrates a screen of the operation panel 21 in the X-ray imaging section 10 according to the first exemplary embodiment. The operation panel 21 has a patient information display field 31 indicating the patient's name etc., an X-ray image display area 32, and a connection method display area 33 indicating the connection method for an image-obtaining timing signal. Additionally, the operation panel 21 has a connection method switching button 34 used to change the connection method, an imaging start button 35 used to give an instruction to start imaging, a message display field 36 indicating a comment etc., and region buttons 37 serving as the target-region selecting unit 25 that allows selection and display of a target region.

When the X-ray generating section 1 and the X-ray imaging section 10 are connected to each other via a dedicated line, the connection method display area 33 indicates "Dedicated line". The connection method switching button 34 provides, for example, a pull-down menu which allows the operator to select a connection method applicable to the X-ray imaging apparatus.

After the operator selects a target region with one of the region buttons 37, a message, such as "Ready for X-ray imaging" is displayed in the message display field 36. Then, by selecting the imaging start button 35, the operator can give an instruction to capture an X-ray image.

Figure 8A:
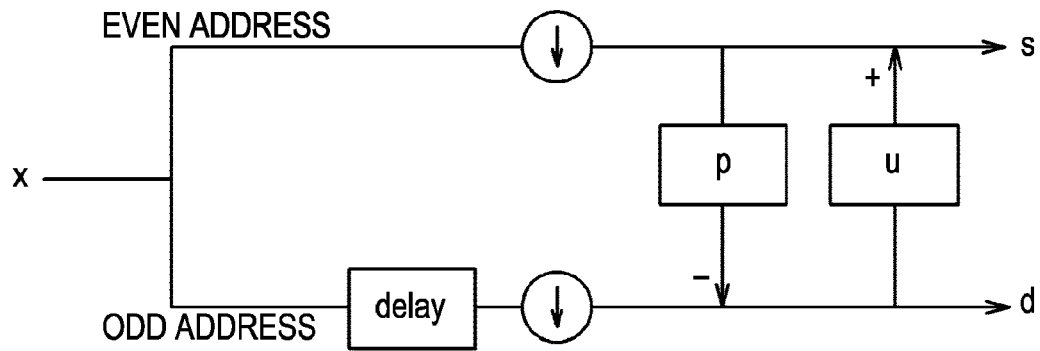
FIG. 8A to FIG. 8C illustrate discrete wavelet transform and inverse transform for noise reduction.
Figure 8B:
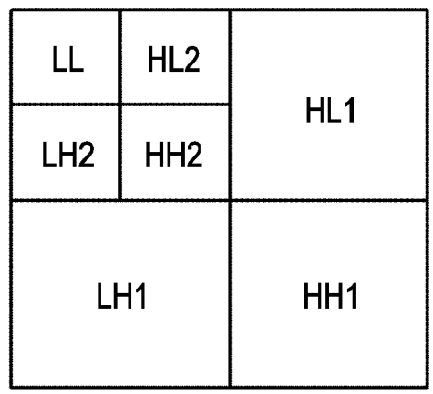
Figure 8C:
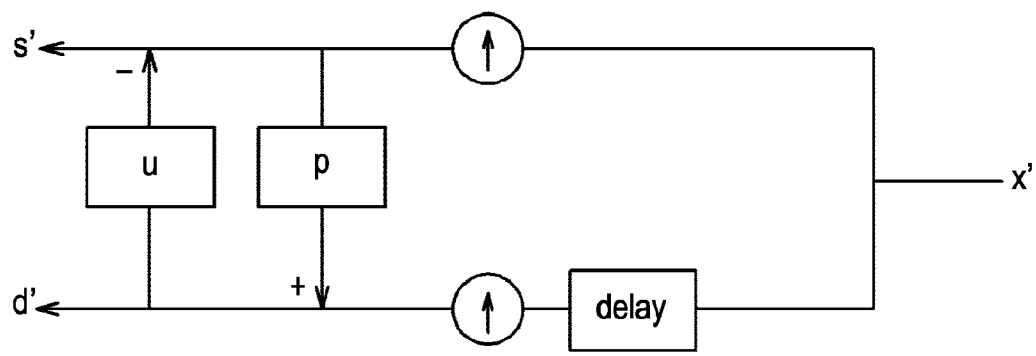

FIG. 8A to FIG. 8C illustrate discrete wavelet transform and inverse transform for noise reduction in the image processing unit 17. FIG. 8A is a circuit diagram illustrating decomposition of an image into a plurality of frequency components. FIG. 8B illustrates a configuration of a group of two-level transform coefficients obtained by two-dimensional transform. FIG. 8C illustrates a reconstruction circuit. Noise reduction decomposes an image into a plurality of frequency components, and analyzes noise superimposed on each of the frequency components to generate noise data. By subtracting noise data from each frequency component, it is possible to reduce noise present in the corresponding frequency band.

In the first exemplary embodiment, even when the stability of communication is reduced, X-ray radiation time can fall within the image accumulation time T of the X-ray imaging apparatus. Since this can be realized by increasing the image accumulation time T, dark current noise may appear in the image. The dark current noise may be caused by variations in the characteristics of photodiodes and amplifiers corresponding to respective pixels, and fixed pattern noise and random noise appear in a mixed manner. The level of dark current noise increases monotonously as the image accumulation time T increases. The dark current noise differs in frequency from an image representing the distribution of X-rays having passed through the subject P. Therefore, by performing frequency decomposition and weighting the corresponding frequency component image with a value obtained by weakening an emphasis coefficient to realize reconstruction, it is possible to reduce negative impacts on image quality.

The dark current noise has a fixed pattern depending on the accumulation time. Therefore, the corresponding frequency components have a certain tendency in an image divided into subbands. If spatial frequencies in noise components increased by an increase in accumulation time correspond to, for example, a frequency subband HH2 of FIG. 8B, the noise reduction according to the first exemplary embodiment suppresses components corresponding to the frequency subband HH2 and sums them up in FIG. 8C. The noise reduction of the first exemplary embodiment can adjust the amount of subtraction, for example, to 10 different levels. By changing a parameter value for adjusting the amount of subtraction, it is possible to suppress noise in the corresponding frequency band.

Thus, by changing the noise reduction in the above-described manner in accordance with a change in drive timing, it is possible to suppress dark current noise and improve image quality.

In the first exemplary embodiment described above, the image accumulation time T of the X-ray imaging apparatus is changed in accordance with the connection state in communication. In a second exemplary embodiment of the present invention, an accumulation table is changed by using not only connection information, but also target region information.

Figure 9:
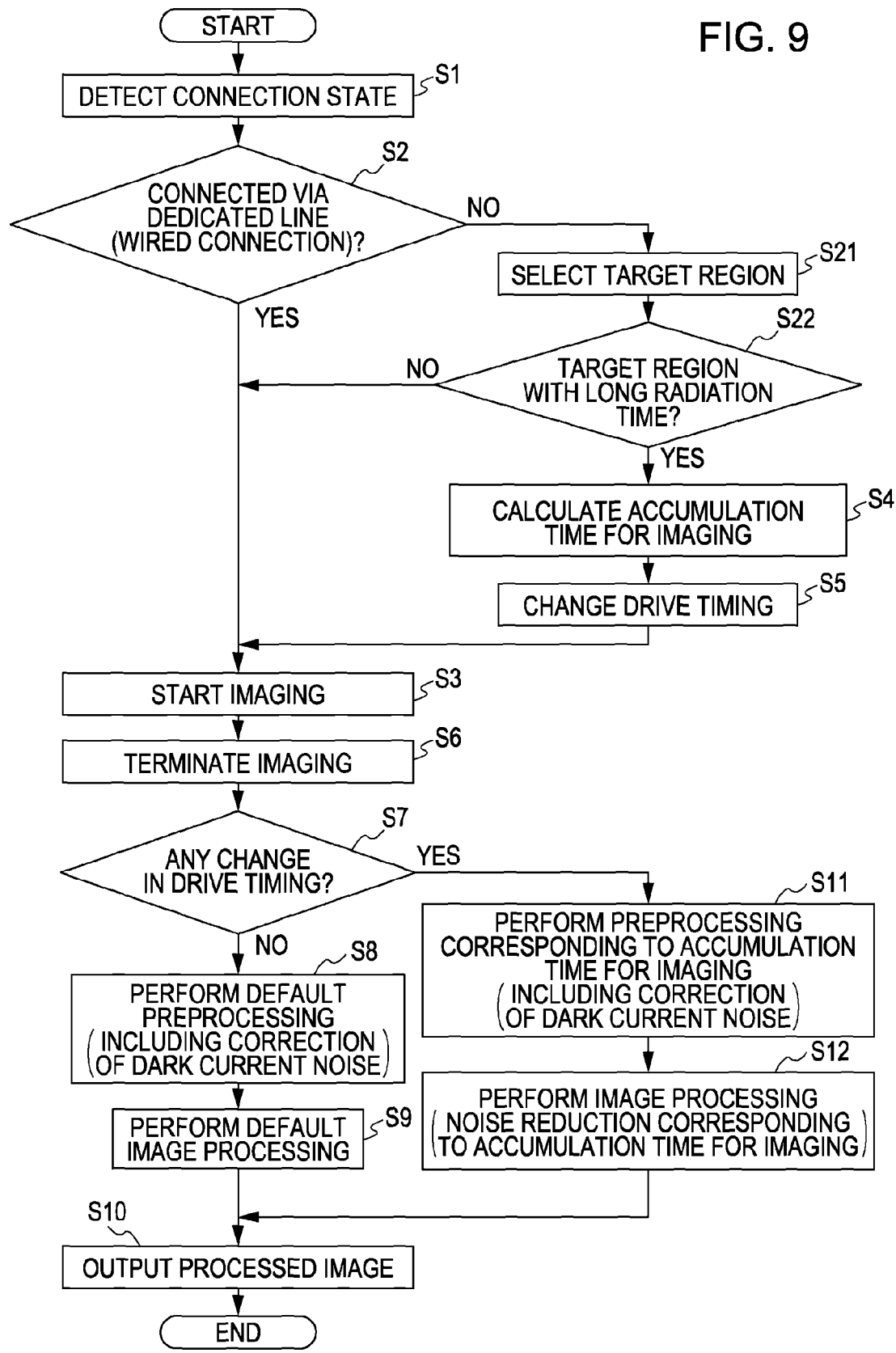
FIG. 9 is a flowchart of a second exemplary embodiment of the present invention.

FIG. 9 is a flowchart illustrating an operation of an X-ray imaging apparatus according to the second exemplary embodiment. In FIG. 9, steps identical to those of FIG. 4 are given the same step numbers and their description will be omitted.

In the second exemplary embodiment, if it is determined in step S2 that the connection is not a wired connection via a dedicated line (No in step S2), the process proceeds to step S21. In step S21, the operator selects, on the operation panel 21, a target region with the target-region selecting unit 25. By selecting a target region whose image is to be captured in imaging, a frequency and gradation appropriate for image processing can be used.

In step S22, a determination is made as to whether the target region selected in step S21 is a region where the amount of X-ray radiation is large. For example, if a lumber side, a hip joint, or a thigh bone is selected, the process proceeds to step S4, where the image accumulation time T for imaging is changed. When, for example, an image of a region near a heart is to be captured, the X-ray radiation time is generally short. Therefore, even when the connection state detected in step S1 shows that the method of communication has less immediacy, it is not very necessary to change the timing for driving the imaging operation of the X-ray imaging apparatus.

In step S22, as described above, the X-ray radiation time is estimated on the basis of the selected target region. However, it is obvious that the second exemplary embodiment is not limited to this. For example, X-ray radiation time input to the X-ray generating section 1 may be obtained by the data collecting unit 15, so that a determination in step S22 as to whether to change the drive timing can be made on the basis of the X-ray radiation time input to the X-ray generating section 1.

Table 1 shows examples of the image accumulation time T and the image processing method corresponding to the connection method (connection state) and the body region according to the second exemplary embodiment. As shown in Table 1, the image accumulation time T of the X-ray imaging apparatus is changed in accordance with the connection method of the X-ray imaging apparatus and the body region.

TABLE 1

| Connection Method | Body Region | X-ray Radiation Time | Image Accumulation Time T | Image Processing Method |
|---|---|---|---|---|
| wireless | chest | 20 ms | 500 ms | image processing 1 |
| wireless | side of thoracic vertebrae etc. | 350 ms | 1000 ms | image processing 2 |
| wired | chest | 20 ms | 500 ms | image processing 1 |
| wired | side of thoracic vertebrae etc. | 350 ms | 500 ms | image processing 1 |

To improve image quality, the image processing method is changed in accordance with a change in image accumulation time T, as shown by numerical values in Table 1.

In the second exemplary embodiment, the image accumulation time T is changed depending on the connection method. When the connection is a wired connection via a dedicated line, the image accumulation time T of the X-ray imaging apparatus and the image processing method are not changed.

In Table 1 above, the connection method is roughly divided into a wired connection and a wireless connection. However, types of connections are not limited to them. For example, the stability of wired communication differs between the case where a dedicated line is used and the case where a general-purpose Ethernet or Gigabit Ethernet connection is used. Additionally, the stability of communication may be determined on the basis of whether the connection is made peer-to-peer or there are collisions from other communications on the network, the packet size for transmission control protocol/Internet protocol (TCP/IP) connection, etc.

In the second exemplary embodiment, a target region is also used as a factor to determine whether the image accumulation time T is to be changed. This is because the probability of occurrence of the problems described above varies depending on the target region. Specifically, this is because the X-ray radiation time and the image accumulation time T vary depending on the target region. For example, when an image of a chest front including a heart is to be captured, since there are many regions that move as the heart moves, the image is typically captured in the shortest possible X-ray radiation time of about 30 to 50 ms, which may vary depending on the maximum rated output of the X-ray generating section 1. To prevent image blur caused by body movement of the subject P during imaging, images of other regions are often captured in a short X-ray radiation time of about 30 to 150 ms.

However, for a target region where the amount of X-rays absorbed by the subject P is large, or for a target region whose image is required to have a high contrast-to-noise ratio, it is necessary to increase the X-ray radiation time. For example, in facilities where the X-ray radiation conditions described above are used, the X-ray radiation time for the lumber side, hip joint, and thigh bone is often about 500 ms. If the accumulation time is 500 ms and the connection is made via a dedicated line, although the image accumulation time T may fall within the X-ray radiation time, an allowance to communication delay is small.

On the other hand, when an image of a region with short X-ray radiation time is to be captured, even if there is a communication delay, it is very likely that the X-ray radiation time can fall within the image accumulation time T, except when the delay is significant. That is, the image accumulation time T is changed in accordance with the target region and the connection method. The target region is selected by the operator with the target-region selecting unit 25 before imaging.

The image processing method in Table 1 is changed in accordance with the target region, accumulation time, and connection method. That is, the image processing method can be determined as a function of the target region, image accumulation time, and wireless or wired connection. When the connection is a wired connection via a dedicated line, the drive method and the image processing method of the X-ray imaging apparatus may be the same as those of the related art.

However, when the connection is made wirelessly, or is made via a general-purpose dedicated line or via dedicated line through a network, there is provided a table for changing the drive method and the image processing method depending on the target region. Changing the drive method and the image processing method is particularly necessary when the lumber side, hip joint, thigh bone, or the like with long X-ray radiation time is selected as a target region. While not shown in Table 1, it is possible to separate "child" and "pregnant woman" from "adult" to change the drive method and the image processing method, accordingly. That is, since it is particularly necessary to prevent children and pregnant women from being unnecessarily exposed to X-rays, it is necessary for them to change the drive method and the image processing method in many regions.

Figure 10:
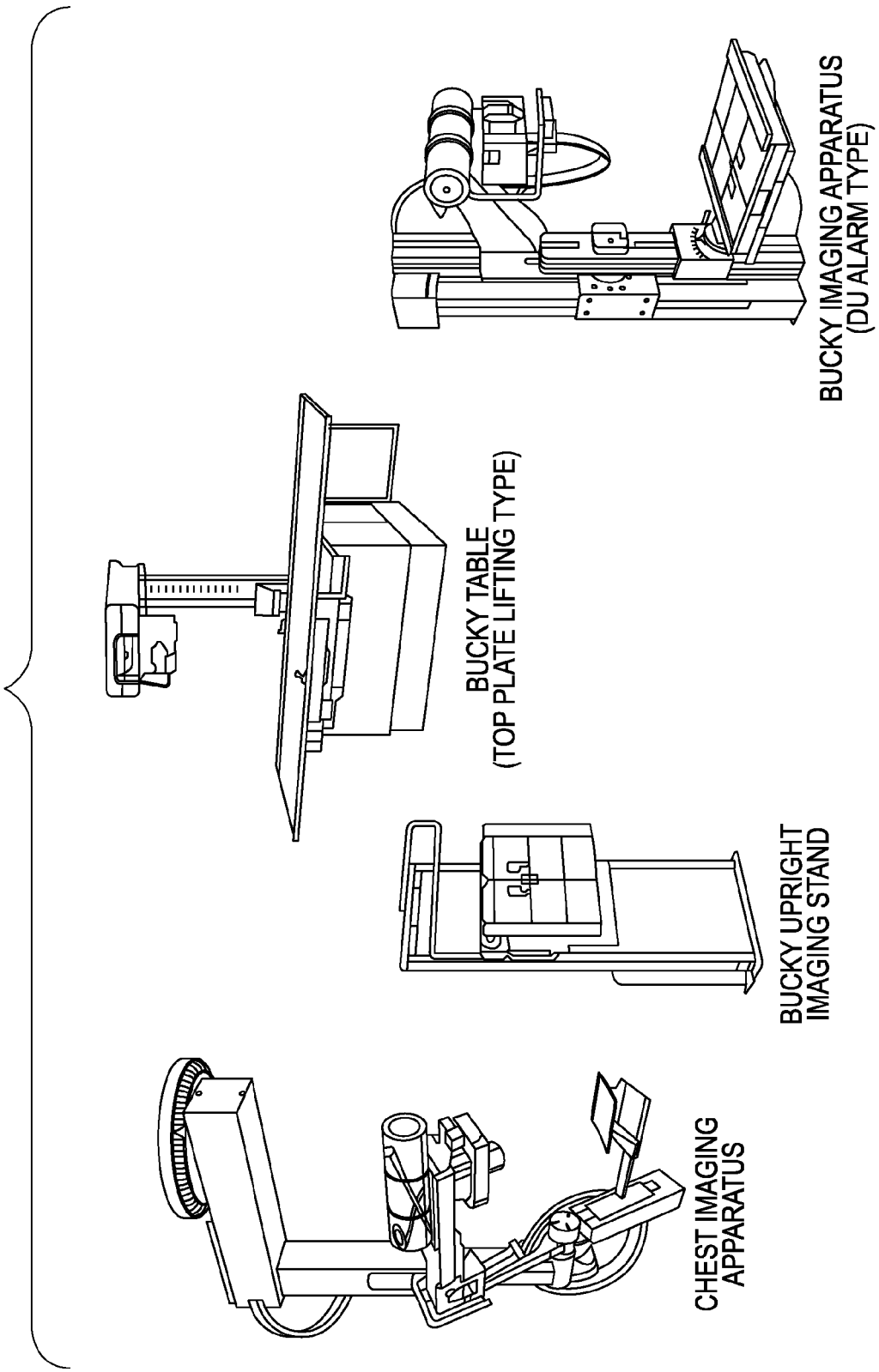
FIG. 10 is a perspective view of examples of imaging systems to which an X-ray imaging apparatus can be attached.

FIG. 10 illustrates examples of various imaging systems to which an X-ray imaging apparatus according to at least one exemplary embodiment of the present invention can be attached. The examples include a head imaging apparatus, a bucky upright imaging stand, a bucky table of top plate lifting type, and a bucky imaging apparatus of DU alarm type.

According to at least one exemplary embodiment of the present invention, in an X-ray imaging apparatus using a plurality of connection methods, the timing of an imaging drive signal, including accumulation time during image acquisition, is changed depending on the connection method. This can improve both communication stability and image quality.

Note that the present invention can be applied to an apparatus including a single device or to a system constituted by a plurality of devices.

Furthermore, the invention can be implemented by supplying a software program, which implements the functions of the foregoing exemplary embodiments, directly or indirectly to a system or apparatus, reading the supplied program code with a computer of the system or apparatus, and then executing the program code. In this case, so long as the system or apparatus has the functions of the program, the mode of implementation need not rely upon a program.

Accordingly, since the functions of the present invention are implemented by computer, the program code installed in the computer also implements the present invention. In other words, the claims of the present invention also cover a computer program for the purpose of implementing the functions of the present invention.

In this case, so long as the system or apparatus has the functions of the program, the program may be executed in any form, such as object code, a program executed by an interpreter, or script data supplied to an operating system.

Examples of storage media that can be used for supplying the program are a floppy disk, a hard disk, an optical disk, a magneto-optical disk, a compact-disk read-only memory (CD-ROM), a CD recordable (CD-R), a CD-rewritable (CD-RW), a magnetic tape, a non-volatile type memory card, a ROM, and a digital versatile disk (DVD) (DVD-ROM and DVD-R).

As for the method of supplying the program, a client computer can be connected to a website on the Internet using a browser of the client computer, and the computer program of the present invention or an automatically-installable compressed file of the program can be downloaded to a recording medium such as a hard disk. Further, the program of the present invention can be supplied by dividing the program code constituting the program into a plurality of files and downloading the files from different websites. In other words, a World Wide Web (WWW) server that downloads, to multiple users, the program files that implement the functions of the present invention by computer is also covered by the claims of the present invention.

It is also possible to encrypt and store the program of the present invention on a storage medium, such as a CD-ROM, distribute the storage medium to users, allow users who meet certain requirements to download decryption key information from a website via the Internet, and allow these users to decrypt the encrypted program by using the key information, whereby the program is installed in the user computer.

Besides the cases where the aforementioned functions according to the exemplary embodiments are implemented by executing the read program by computer, an operating system or the like running on the computer may perform all or a part of the actual processing so that the functions of the foregoing exemplary embodiments can be implemented by this processing.

Furthermore, after the program read from the storage medium is written to a function expansion board inserted in the computer or to a memory provided in a function expansion unit connected to the computer, a CPU or the like mounted on the function expansion board or function expansion unit performs all or a part of the actual processing so that the functions of the foregoing exemplary embodiments can be implemented by this processing.

As many apparently widely different exemplary embodiments of the present invention can be made without departing from the spirit and scope thereof, it is to be understood that the invention is not limited to the specific exemplary embodiments thereof except as defined in the appended claims.

This application claims the benefit of Japanese Patent Application No. 2008-201430 filed Aug. 5, 2008, which is hereby incorporated by reference herein in its entirety.

What is claimed is:

1. An X-ray imaging apparatus comprising:
   an X-ray imaging section including a two-dimensional X-ray imaging unit that receives X-rays having passed through a subject;
   an X-ray generation control unit;
   a communication connection unit between the X-ray imaging section and the X-ray generation control unit;
   a detecting unit configured to detect a connection method of the communication connection unit; and
   a drive-method changing unit configured to change the drive method of the X-ray imaging section depending on the connection method detected by the detecting unit,
   wherein when the connection method detected by the detecting unit includes a connection via a dedicated line, the drive-method changing unit changes the drive method to a method in which an image is obtained during fixed image accumulation time, and when the connection method detected by the detecting unit includes a connection wirelessly or via a wired connection that is not via a dedicated line, the drive-method changing unit changes the drive method to a method in which image accumulation time is determined in synchronization with the X-ray generation control unit.

2. The X-ray imaging apparatus according to claim 1, further comprising a target-region selecting unit configured to select a target region whose image is to be captured,
   wherein the drive-method changing unit is arranged to change the drive method on the basis of information about the target region selected by the target-region selecting unit.

3. The X-ray imaging apparatus according to claim 1, wherein the drive-method changing unit is arranged to change image accumulation time of the X-ray imaging section.

4. The X-ray imaging apparatus according to claim 3, arranged to change an image processing method in accordance with a change in image accumulation time of the X-ray imaging section.

5. The X-ray imaging apparatus according to claim 4, arranged to change the image processing method by changing a dark current correcting method.

6. The X-ray imaging apparatus according to claim 4, arranged to change the image processing method such that a dark current in an image is corrected by obtaining a dark current image corresponding to the image accumulation time, selecting an image for dark current correction, and subtracting the selected image from an X-ray image.

7. The X-ray imaging apparatus according to claim 6, arranged to change the image processing method by changing a method of noise reduction.

8. The X-ray imaging apparatus according to claim 7, arranged to change the method of noise reduction by changing emphasis coefficients corresponding to a plurality of specific frequency images in the noise reduction.

* * * * *